(12) United States Patent
Crockatt et al.

(10) Patent No.: US 11,725,014 B2
(45) Date of Patent: Aug. 15, 2023

(54) CONTINUOUS PROCESS FOR CYCLOADDITION REACTIONS

(71) Applicant: Nederlandse Organisatie voor toegepast-natuurwetenschappelijk onderzoek TNO, s-Gravenhage (NL)

(72) Inventors: Marc Crockatt, Hertogenbosch (NL); Leonard Ferdinand Gerard Geers, Valkenburg (NL); Johan Urbanus, The Hague (NL); Rudolf Gijsbertus Van Someren, Nieuwegein (NL); Jan Cornelis Van Der Waal, Delft (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 457 days.

(21) Appl. No.: 16/753,048

(22) PCT Filed: Oct. 3, 2018

(86) PCT No.: PCT/NL2018/050657
§ 371 (c)(1),
(2) Date: Apr. 2, 2020

(87) PCT Pub. No.: WO2019/070123
PCT Pub. Date: Apr. 11, 2019

(65) Prior Publication Data
US 2020/0239492 A1 Jul. 30, 2020

(30) Foreign Application Priority Data
Oct. 3, 2017 (EP) .................................... 17194633

(51) Int. Cl.
*B01J 19/06* (2006.01)
*B01J 19/00* (2006.01)
(Continued)

(52) U.S. Cl.
CPC ............ *C07D 493/18* (2013.01); *B01J 4/001* (2013.01); *B01J 14/00* (2013.01); *B01J 19/0013* (2013.01);
(Continued)

(58) Field of Classification Search
CPC ...... C07D 493/18; C07D 307/60; B01J 4/001; B01J 14/00; B01J 19/0013; B01J 19/06; B01J 2219/00033; B01J 2219/00119
(Continued)

(56) References Cited

U.S. PATENT DOCUMENTS

2017/0001940 A1 * 1/2017 Sookraj ................ C07D 307/60

FOREIGN PATENT DOCUMENTS

| CN | 105949438 A | * | 9/2016 | ............ C07D 491/22 |
| WO | WO-2016190317 A1 | * | 12/2016 | ............ C07C 69/757 |

(Continued)

OTHER PUBLICATIONS

Harvey A. P. et al: "Operation and Optimization of an Oscillatory Flow Continuous Reactor", Industrial & Engineering Chemistry Research, vol. 40, No. 23, Jul. 3, 2001 (Jul. 3, 2001), pp. 5371-5377, XP093022073, ISSN: 0888-5885, DOI: 10.1021/ie0011223.

*Primary Examiner* — Huy Tram Nguyen
(74) *Attorney, Agent, or Firm* — Banner & Witcoff, Ltd.

(57) ABSTRACT

The invention is directed to a process for the continuous preparation of a cycloadduct product from the reaction of a furanic with a dienophile, comprising heating a first liquid feed stream comprising the dienophile and a solvent in which the dienophile is dissolved; providing a second liquid feed stream comprising the furanic; leading the first liquid feed stream and the second liquid feed stream into a continuous reactor to produce a product solution stream comprising the cycloadduct product; and leading the product solution stream to an product isolation zone to produce an
(Continued)

isolated cycloadduct product. A further aspect of the invention is an apparatus for carrying out this reaction.

16 Claims, 2 Drawing Sheets

(51) Int. Cl.
    *B01J 14/00*     (2006.01)
    *C07D 493/18*     (2006.01)
    *B01J 4/00*     (2006.01)

(52) U.S. Cl.
    CPC ...... *B01J 19/06* (2013.01); *B01J 2219/00033* (2013.01); *B01J 2219/00119* (2013.01)

(58) Field of Classification Search
    USPC .......................................................... 549/237
    See application file for complete search history.

(56) References Cited

FOREIGN PATENT DOCUMENTS

| | | | | |
|---|---|---|---|---|
| WO | 2017004349 A2 | 1/2017 | | |
| WO | WO-2017146581 A1 * | 8/2017 | ........... | C07C 249/12 |

\* cited by examiner

CONTINUOUS PROCESS FOR CYCLOADDITION REACTIONS

RELATED APPLICATIONS

This application is a National Stage Application under 35 U.S.C. 371 of co-pending PCT application PCT/NL2018/050657 designating the United States and filed Oct. 3, 2018; which claims the benefit of EP application number 17194633.8 and filed Oct. 3, 2017 each of which are hereby incorporated by reference in their entireties.

FIELD OF THE INVENTION

The invention is in the field of chemical processes. In particular, the invention is directed to a continuous process for the cycloaddition reaction of a furanic with a dienophile.

BACKGROUND OF THE INVENTION

In the recent years, interest in furanic compounds as intermediate chemical compounds for the production of chemicals from biomass has increased considerably. Of particular interest is the production of renewable aromatics from furanics by a cyclo-addition or Diels-Alder reaction with dienophiles. Depending on their specific substitution pattern, these aromatics can conveniently be used for production of a wide range of mass consumption products, such as plasticizers, synthetic fibers, (plastic bottles), fire-retardant materials, resins and the like. To this end, the reactions of a variety of different furanics with dienophiles have been investigated.

For instance, Mahmoud et al. *Green Chemistry*, 2014, 16, 167-175 discloses the reaction of furan and maleic anhydride (MA) to phthalic anhydride, Van Es et al. *Angew. Chem. Int. Ed.* 2016, 55, 1368-1371 discloses the reaction of 2-methylfuran (2-MF) and MA, and Van Es et al. ChemSusChem 2015, 8, 3052-3056 discloses the reaction of 2-MF or 2,5-dimethylfuran (2,5-DMF) and MA.

A drawback of the known methods for the cycloaddition of furanics with dienophiles is that these methods are carried out batch-wise, which makes it challenging to scale-up these processes to commercially viable processes. It is therefore desired to provide a continuous process for the cycloaddition process. In WO 2017/004349, a continuous process is suggested, but this process is found not to be suitable for the reaction due to problems associated with the solubility, product stability, and the desired purity of the cycloaddition product.

It is desired that the obtained cycloaddition product be obtained in a high enough purity to prevent or at least limit degradation of the product due to polymerization and other degradation processes caused by the presence of impurities in following reactions. The presence of impurities can typically be observed by coloration of the product, and significant levels of impurities lead to coloration of the products of following reactions, leading to increased challenge and cost to achieve the purity levels desired, and required, by industry.

SUMMARY OF THE INVENTION

The present inventors found that one or more of the above-mentioned drawbacks can be addressed by a continuous process wherein the dienophile and the furanic are fluidic, for instance by dissolving either one or both in a solvent, and subsequently reacting the dienophile with the furanic in a continuous reactor to produce the cycloaddition product, and wherein the cycloaddition product is maintained in solution in the continuous reactor and subsequently isolated in an isolation zone.

Accordingly, the present invention is directed to a process for the continuous preparation of a cycloadduct product from the reaction of a furanic with a dienophile, comprising:
 heating a first liquid feed stream comprising the dienophile and optionally a solvent in which the dienophile is dissolved;
 providing a second liquid feed stream comprising the furanic;
 leading the first liquid feed stream and the second stream into a continuous reactor to produce a product solution stream comprising the cycloadduct product;
 leading the product solution stream to a product isolation zone to produce an isolated cycloadduct product.

By heating the first liquid feed stream, the dienophile can be maintained dissolved in the solvent or melted as a fluid. This is particularly beneficial since a slurry or suspension of typical dienophiles such as maleic anhydride can comprises large diameter particles of the maleic anhydride, leading to clogging of the continuous process. A melt of the dienophile can be for instance obtained by heating, or milling and heating. For instance, maleic anhydride, a preferred dienophile, will melt when heated to about 55° C. However, melting and or milling is less desirable since this adds extra handling, and therefore costs, and the solid dienophiles are generally hygroscopic, such that they tend to clump together even after milling. As such the presence of the solvent, and the use of a dienophile solution, is preferred.

In a preferred embodiment, the dienophile is dissolved in the solvent and the first liquid feed stream is maintained at a temperature above the crystallization temperature of the dienophile in said solvent.

A typically use of the solvent is to ensure that impurities are removed in the isolation, in particular if this comprises crystallization (vide infra). Accordingly, the solvent may be added with the first liquid feed stream, the second liquid feed stream and/or as a third feed stream into the reactor.

A particular advantage of heating the first liquid feed stream is that the reaction may be carried out at an elevated temperature (i.e. above room temperature). To further reduce the residence time of the streams in the process, it may be preferably that the continuous reactor is heated or thermally isolated to quickly achieve equilibrium, and then produce the isolated cycloadduct product (e.g. cooled to crystallize, vide infra) in order to pull the reaction equilibrium toward the side of the cycloaddition product. Thus, a particular advantage of including the cycloadduct product isolation in the present process is that the equilibrium of cycloaddition reactions can be shifted more towards to the side of product formation by continuously removing the product.

A typical dienophile that can be used in the process of the present invention is selected from the group consisting of maleic anhydride, maleic acid, maleate esters, fumaric acid, fumarate esters, maleimides, acrylic acid, acrylate esters, acrolein. Preferably the dienophile is maleic anhydride. The present process may include a step of producing the dienophiles in situ from a pre-dienophile. For instance, succinic acid (a pre-dienophile) can be oxidized to maleic acid or maleic anhydride in situ, and then reacted with the furanic.

Suitable solvents include solvents selected from the group consisting of ethers, esters, aromatics, heteroaromatics, aliphatics, nitriles, ketones, alcohols, amides, sulfoxides, nitrated and chlorinated aliphatics, and nitrated and chlorinated aromatics. Preferably, the solvent is an ether, either methyl tert-butyl ether, cyclo-pentyl methyl ether or diethyl ether. The furanic may also suitably be used as the solvent in which the dienophile is dissolved in the first solution feed stream.

In the embodiment wherein the dienophile is maleic anhydride and the solvent is methyl tert-butyl ether, the weight ratio of dienophile to solvent in the first liquid feed stream is preferably in the range of 10:1 to 1:10, more preferably in the range 5:1 to 1:5, and most preferably in the range 2:1 to 1:2. Such a ratio may also be suitable for other dienophile and solvent combinations.

Although the temperature above the crystallization temperature of the dienophile in the solvent inter alia depends on the specific solvent and the dienophile, as well as the concentration, the temperature of the first liquid feed stream is typically maintained in the range of 30 to 100° C., preferably in the range of 40-70° C.

It is further preferred that the second liquid feed stream comprising the furanic is also heated. More preferably, the second liquid feed stream is heated at the same temperature as the first liquid feed stream. This prevents or at least limits the drop of temperature when the first liquid feed stream and the second liquid feed stream are contacted, such that all compounds remain in solution. It is further preferred that the first liquid feed stream, the second liquid feed stream, and the product solution stream are maintained at an elevated temperature throughout the process up to the product isolation zone, to maintain the furanic, the dienophile and the cycloadduct product in solution or fluidic.

In a typical embodiment, heating the second liquid feed stream is carried out by heating it just before it enters into the continuous reactor. It may however, also be possible to add the second liquid feed stream at ambient temperature and using the exotherm of the reaction (i.e. the heat generated by the reaction) to maintain everything in solution.

Most preferably, the first liquid feed stream, the second liquid feed stream, and the product solution stream are maintained at an equal elevated temperature throughout the process up to the product isolation zone. This minimizes temperature fluctuation in the process that can lead to side reactions and/or undesired precipitation of the starting materials and/or product.

The present process is particularly suitable for furanics according to structure I

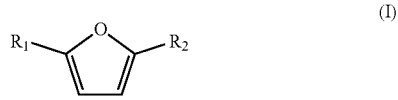

(I)

wherein $R_1$ and $R_2$ are independently selected from the group consisting of H, $CH_3$, $CH_2OH$ and esters and ethers thereof, $CO_2H$ and esters thereof, and amides and tertiary amines of $CH_2NH_2$. Preferably the furanic of the present invention comprises furan, 2-methylfuran and/or 2,5-dimethylfuran.

For some furanics and/or dienophiles in accordance with the present invention, it may be preferred to catalyze the reaction thereof with a catalyst. For instance, the reaction of 2,5-dimethylfuran with methyl acrylate is preferably catalyzed. Accordingly, the first solution feed stream and/or the second liquid feed stream may further comprise the catalyst. The catalyst may also be provided to the continuous reactor as a stream separate for said two feed streams, for instance together with the third stream comprising the solvent, if present, or as an additional stream. Typical catalysts that are suitable to catalyze the reaction in accordance with the present invention include acids and Lewis acids. Catalysts that suitably catalyze the reaction in batch processes can typically be applied for the present invention, although it may be preferred to modify the catalyst for continuous processes. The catalyst may for instance comprise an immobilized catalyst or a soluble catalyst.

In general, the furanic is liquid at typical reaction temperatures (e.g. in the range of 20 to 100° C., preferably in the range of 40-70° C.) and therefore does not necessarily require to be dissolved in a solvent to be fluidic. However, in certain embodiments it may be preferred to dissolve the furanic in a solvent, more preferably in the same solvent in which the dienophile is dissolved as well and/or a solvent from which the product can be cleanly crystallized in a high yield. Such a solvent can routinely be selected. Dissolving the furanic may be beneficial to generally improve the processing, such as to lower the viscosity of the second liquid feed stream, to ensure solution of any impurities in the feed, to ensure solution throughout reaction, or to affect the crystallization.

A typical reaction, for example with maleic anhydride (MA) and the furanic according to compound I as defined herein-above, that can suitably be carried out with the present process is illustrated with Scheme 1 below.

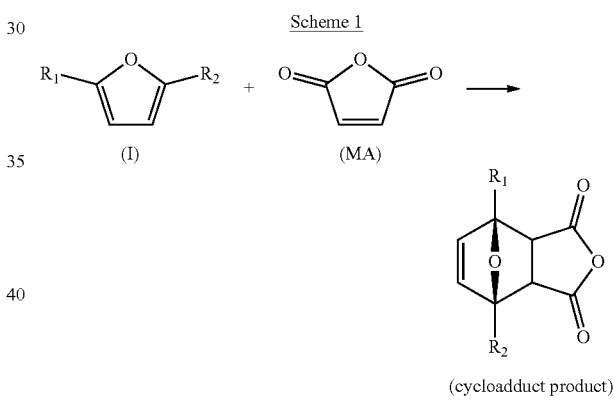

Reactions with other suitable dienophiles proceed similarly and result in corresponding cycloadduct products. The cycloadduct products are generally solid at room temperature or temperatures not far below room temperature (for instance at about 0° C.) and can therefore suitably be isolated by crystallization. Accordingly, in a preferred embodiment, producing the isolated cycloadduct product comprises crystallization and solid-liquid separation of the cycloadduct product. To this end, the solvent in which the dienophile is dissolved in the first liquid feed stream is preferably a solvent in which the cycloadduct product can crystallize.

The product isolation zone may be a product isolation device (vide infra) and/or be integrated in the continuous reactor. For instance, in a plug flow reactor a section can be dedicated to the reaction, whereas a next section can be cooled, to induce crystallization.

In an embodiment wherein the product isolation zone is integrated into the continuous reactor, the reactor may comprise at the product isolation zone a cooling device and/or a anti-solvent inlet to induce or promote crystallization. Alternatively, or additionally, the reactor may comprise at the product isolation zone a device to induce ultrasound, high shear and/or Non-Photochemical Laser Induced Nucleation (NPLIN).

To facilitate the crystallization of the cycloadduct product, the product solution stream may be cooled upon entering the product isolation zone. Alternatively, or additionally, the product solution stream may be concentrated and/or be mixed with an anti-solvent to promote the crystallization of the cycloadduct product. Alternatively, or additionally, the crystallization may be promoted or initiated by seeding and/or ultrasound. In a typical embodiment, cooling and seeding is combined to crystallize the cycloadduct product.

A further aspect of the present invention is an apparatus for the continuous preparation of the cycloadduct product in accordance with the present invention, said apparatus comprising:
- a first feed vessel (1) comprising a first feed outlet (11) and a first heating device (10);
- a second feed vessel (2) comprising a second feed outlet (21) and preferably a second heating device (20);
- a continuous reactor (3) comprising a reactor inlet (32) that is connected to the first and the second feed outlets (11,21) and further comprising a reactor outlet (31) and preferably a third heating device (30); and
- a product isolation zone comprising a product inlet (42) that is connect to the reactor outlet (31) and further comprising a product outlet (41) and optionally a further output for residual liquids.

DETAILED DESCRIPTION OF THE INVENTION

Figure 1:
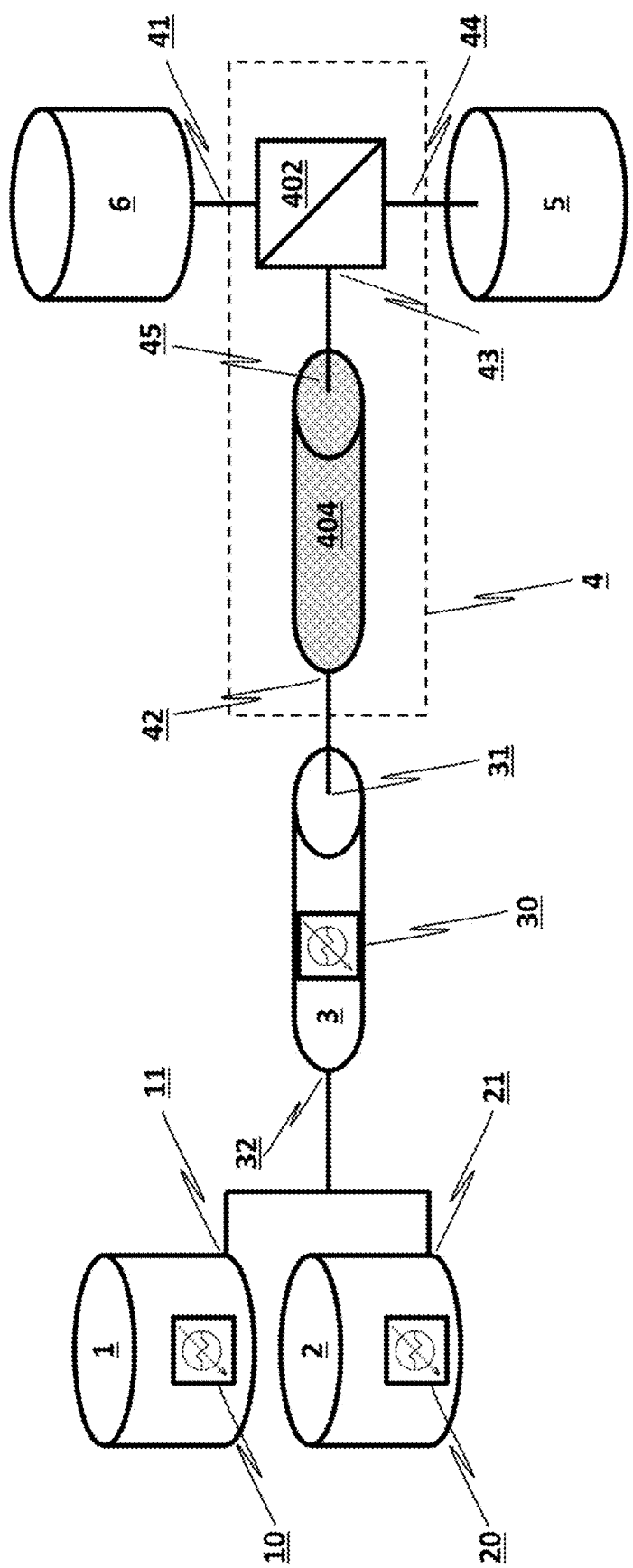
FIG. 1 is a schematic of an apparatus according to an embodiment of the invention. The apparatus comprises a product isolation zone (4) comprising a product inlet (41) that is connected to the reactor outlet (31), a continuous crystallization device (404) with a solid-liquid product outlet (45) that is connected to a solid-liquid product inlet (43) of a solid-liquid separation device (402) which further comprises the product outlet (41) that is connected to the product vessel (5) and a liquid output (44) that is connected to a filtrate vessel (6).

In a particular embodiment, as illustrated in FIG. 1, the apparatus comprises a product isolation zone (4) comprising a product inlet (41) that is connected to the reactor outlet (31), a continuous crystallization device (404) with a solid-liquid product outlet (45) that is connected to a solid-liquid product inlet (43) of a solid-liquid separation device (402) which further comprises the product outlet (41) that is connected to the product vessel (5) and a liquid output (44) that is connected to a filtrate vessel (6).

In a preferred embodiment, a mixing zone is present between the first and second feed outlets (11,21) and the inlet (32) of the continuous reactor to combine and mix the first liquid feed stream and the second liquid feed stream before these streams are lead into the reactor. The mixing zone may comprise an active mixer (i.e. a device to which external energy is supplied to achieve mixing, for instance a mixing chamber/vessel with stirrer or rotor/stator), a flow diffusion/passive flow mixer (e.g. a device having a geometry adapted to encourages mixing of two entering feed streams), or a static mixer (i.e. a device that is adapted to homogenize multiple fluids but while being free of moving parts). Examples of active mixers include CSTRs and ultra-turraxes. Examples of flow diffusion/passive flow mixers include T-mixers, Y-mixers, and vortex-type mixers. Examples of static mixers include those which contain physical internals to effect flow movement, such as baffles, helical inserts, or other types of packing, and those which contain no internals and utilize the shape of reactor and flow velocity to achieve internal mixing, such as the Dean-Vortices which are achieved in certain flow regimes in a helical shaped tubular reactor.

Examples of suitable continuous reactors comprise continuous stirred-tank reactors (CSTR), fluidized bed reactors, spinning disc reactors (SDR), an optionally pulsed helical tube reactor, an optionally pulsed oscillating baffled reactor (OBR) and/or plug flow reactors (PFR). The continuous reactor may comprise a helical plug flow reactor, which may particularly be beneficial if there is no static mixer present such that the helical structure provides for the mixing zone and the reaction zone. However, since the first and second feed streams are fluids, and not suspensions, the presence of Dean-Vortices to promote the reaction is not required.

Figure 2:
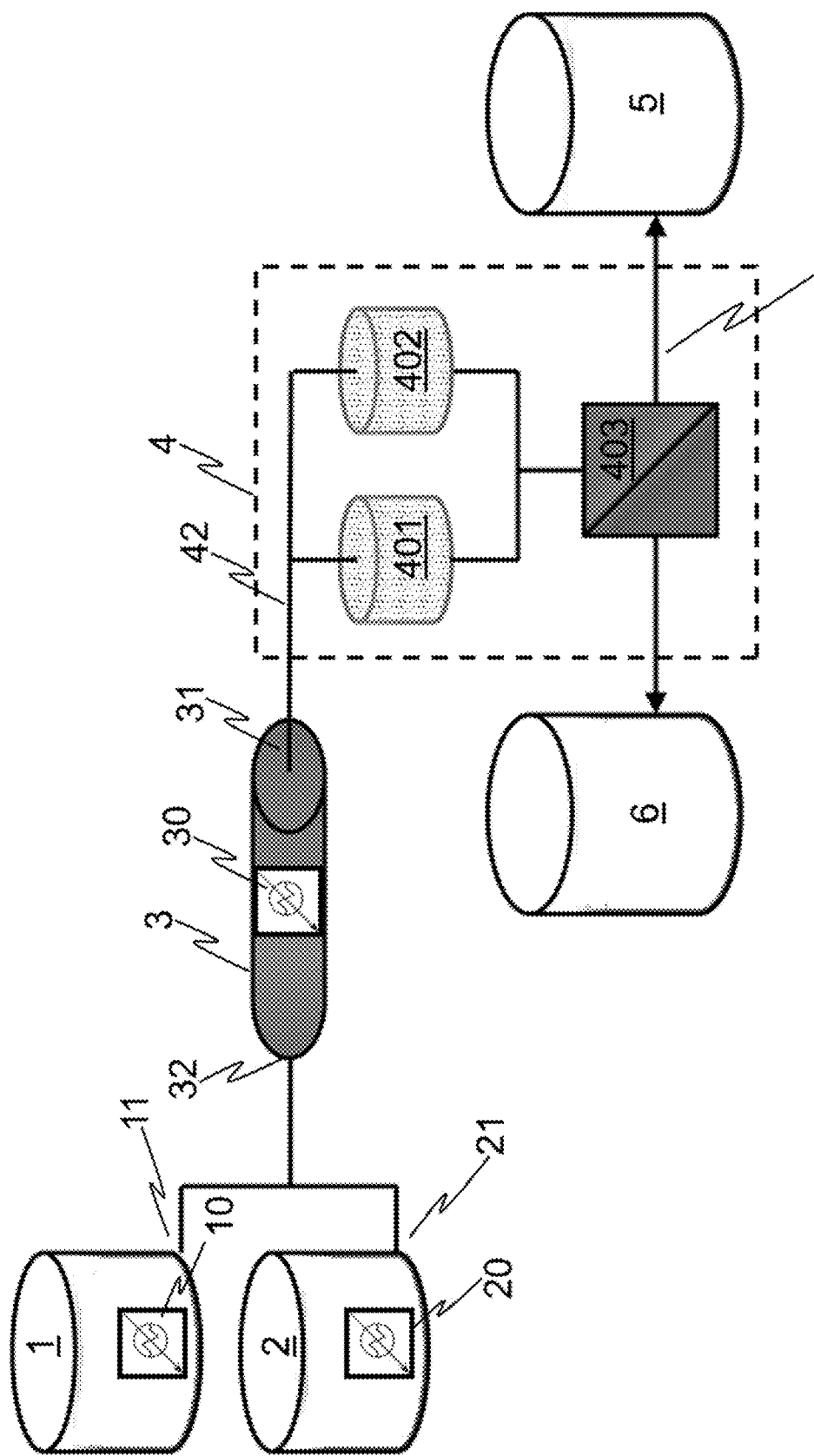
FIG. 2 is a schematic of an apparatus according to another embodiment of the invention. In this embodiment wherein the isolation of the cycloadduct product comprises crystallization, it is particularly preferred that the product isolation zone (4) comprises a crystallization system that enables (semi-)continuous crystallization, for instance a crystallization device that comprises at least two crystallization devices (401,402) that are in parallel which are connected to the reactor outlet (31) and to the solid-liquid separation device (403) that comprises said product outlet (41).

In the embodiments wherein the isolation of the cycloadduct product comprises crystallization, it is particularly preferred that the product isolation zone (4) comprises a crystallization system that enables (semi-)continuous crystallization, for instance a crystallization device that comprises at least two crystallization devices (401,402) that are in parallel which are connected to the reactor outlet (31) and to the solid-liquid separation device (403) that comprises said product outlet (41). This embodiment is illustrated in FIG. 2. The crystallization devices may also be connected in series to afford a continuous mixed-suspension mixed-product removal (MSMPR) crystallization device.

Typical crystallization devices are operated in a semi-continuous manner and providing at least two crystallization units that can alternately be operated, enables the overall process to proceed continuously. The isolated cycloadduct product can after a solid-liquid separation (e.g. filtration) be washed with an appropriate solvent and temporarily stored in a product storage vessel (5) that is connected to the outlet of the product isolation zone. The residual liquid can be stored in a liquid storage vessel (6) and recycled to recover residual product from the product solution stream.

In particular embodiments, the crystallization device comprises a Archimedean screw-type crystallizer device, a fluidized bed crystallizer (FBC), a plug-flow crystallizer (PFC), a spinning disk crystallizer (SDC), and/or or a tubular device, with or without internal mixing.

In the embodiments wherein the isolation zone contains a solid-liquid separation device (e.g. a filtration device) to separate the crystallized cycloadduct product from the remaining liquids, it is particularly preferred that the product isolation zone (4) comprises a device adapted for (semi-)continuous solid-liquid separation (402) which is connected to the outlet of the crystallization device. For example, a solid-liquid separation device which comprises two standard pressure/vacuum filter units in parallel would facilitate semi-continuous separation by affording the ability to empty one filter while the second filter is being filtered, and vice versa. This type of configuration also provides the ability to wash the cycloadduct product in situ. More preferably, a continuous solid-liquid separation device is applied. Examples of this include drum filters, belt filters, wash columns, and liquid/solid centrifuges. In these cases, washing of the cycloadduct product may be carried ex situ to the filter device.

As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features.

For the purpose of clarity and a concise description features are described herein as part of the same or separate embodiments, however, it will be appreciated that the scope of the invention may include embodiments having combinations of all or some of the features described.

The invention can be illustrated by the following non-limiting examples.

EXAMPLE 1

Continuous Process

In a device as illustrated in FIG. 2, the first feed vessel (1) is charged with the solvent methyl tert-butyl ether (MTBE) and the dienophile maleic anhydride in a 1:1 weight ratio. The vessel is then heated to 45° C. and the mixture is stirred until solution was achieved. The second feed vessel (2) is charged with the furanic 2-methylfuran.

The pumps for both feed vessels are started, in a 2.34:1 volumetric ratio, corresponding to a 1:1 molar ratio of maleic anhydride:2-methylfuran. The flow from the second feed vessel is warmed to 45° C. before the two streams were contacted at the mixing point, which was a static mixer with internals.

The mixed flow is then passed through a helical plug flow reactor (3) which is also heated to 45° C. The reactor volume is chosen so as to allow for around 15 minutes of residence time in the reactor.

The yellow/orange-colored reaction mixture containing the cycloadduct product (1-methyl-7-oxabicyclo[2.2.1]hept-5-ene-2,3-dicarboxylic anhydride, i.e. compound according to structure 1 wherein $R_1$=Me and $R_2$=H) is then maintained at 45° C. and fed into crystallizer 1 (401) which is set to a temperature of 45° C. When crystallizer 1 is full, the flow is diverted to crystallizer 2 (402) which is set to a temperature of 45° C. As crystallizer 2 is filled with reaction mixture, a cooling gradient is applied to crystallizer 1, bringing the temperature of the contents to between 0 and 20° C. over a period of 0.5-20 hours. When the temperature of the contents is between 35-40° C., crystallization is initiated by seeding with product isolated from a previous run (In following crystallizations, residual product in the crystallizer acts as seed, and thus seeding is only required in later crystallizations if there is no seed crystals in the crystallizer after filtering.). Once the desired temperature is reached, the mixture is stirred for a further 30 minutes. The resulting slurry is then transferred to the filter (403), where the liquid is removed by filtration. After this, and when crystallizer 2 is full, the cooling/seeding (if required)/crystallization/filtration/washing process is repeated for crystallizer 2 while crystallizer 1 (set to 45° C.) is filled with reaction mixture.

In this way, the process is run continuously until the desired amount of product had been generated. After the majority of the liquid has been removed from the solid in the filter (403). Prior to removing the solid from the filter (403), a suitable amount of methyl tert-butyl ether, cooled to the same temperature as the slurry has been prior to filtration, is used to wash the solid which has been collected, with the liquids again being removed by filtration. Optionally, if the run is complete and there is residual solids in the crystallisers and tubings to the filter, then Crystallizers 1 and/or 2 are charged with a suitable amount of methyl tert-butyl ether, and this is cooled to the same temperature as the slurry had been prior to filtration. The methyl tert-butyl ether in the crystallizer(s) is used to rinse the tubing, and wash the product solid. The washing process is repeated as required to remove residual starting materials and other impurities from the product solid. The filtrates and washes are collected together in the filtrate vessel (6). 1-methyl-7-oxabicyclo[2.2.1]hept-5-ene-2,3-dicarboxylic anhydride is isolated as a white/off-white solid.

EXAMPLE 2

Investigation of Effect of Heating

In a batch setup, three reactions (2a, 2b and 2c) were performed:

2a. MTBE (10 ml) and maleic anhydride (MA) (3000 mg) were mixed at room temperature for 3 hours, at which point the mixture was a white suspension, and the MTBE was saturated with MA. 5 ml of the solution was then pipetted out and into a separate reactor. The remaining MTBE/MA suspension was then reduced to dryness by rotary evaporation, leaving 2323 mg of residual MA. As such, the saturated solution in the reactor contained 677 mg of MA in MTBE (~135 mg/ml). The solution in the reactor was stirred and then to this was added 1 molar equivalent of furan. The mixture was stirred for 2 hours and remained a colourless solution, but a white solid precipitated on stirring overnight. This was isolated by filtration, and dried to yield very pure, white, furan-MA Diels-Alder adduct in 20.7% yield.

2b. A 1:1 ratio (by weight) of MA and MTBE were heated to 45° C. with mixing to achieve a colorless solution with a concentration of 740 mg MA/ml MTBE, and then 1 molar equivalent of furan (relative to MA) was added. The mixture was heated at 45° C. for a further 15 minutes then allowed to cool to room temperature, which induced precipitation (as per Example 1) of a white solid. This was isolated by filtration, and dried to yield very pure, white, furan-MA Diels-Alder adduct in 79.3% yield.

2c. Furan and MA were mixed in a 1:1 ratio at room temperature without solvent. The reaction started as a suspension and this remains so for at least the first 2 hours at room temperature. After overnight stirring the mixture had solidified and the reactor had to be broken to remove the mixture from the reactor. Unreacted maleic anhydride remained present in the solidified mixture. Isolated yield is 80.1% by weight (not corrected for the maleic anhydride present) as a slightly off white solid (grey in color).

The above results demonstrate that high yields in solution can be obtained by preheating MA in solution to an elevated temperature of 45° C., while performing the reaction neat at room temperature results in a solidified mixture that is not suitable for large scale (continuous) processing.

The invention claimed is:

1. A continuous process for the preparation of a cycloadduct product from the reaction of a furanic with a dienophile, comprising:

heating a first liquid feed stream comprising the dienophile and a solvent in which the dienophile is dissolved in a weight ratio of the dienophile to solvent in the range of 10:1 to 1:10, to provide a heated first liquid feed stream at an elevated temperature between 30° C. to 100° C.;

heating a second liquid feed stream comprising the furanic;

leading the heated first liquid feed stream at the elevated temperature and the heated second liquid feed stream at the elevated temperature into a continuous reactor to produce a product solution stream comprising the cycloadduct product; and leading the product solution stream to a product isolation zone to produce an isolated cycloadduct product comprising crystallization by cooling and seeding;

wherein the first liquid feed stream, the second liquid feed stream, and the product solution stream are maintained at an elevated temperature throughout the process up to the product isolation zone, to maintain the furanic, the dienophile and the cycloadduct product in solution and/or fluidic.

2. The process in accordance with claim 1, wherein the furanic comprises a compound according to structure I

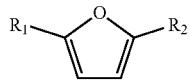

(I)

wherein $R_1$ and $R_2$ are independently selected from the group consisting of H, $CH_3$, $CH_2OH$ and esters and ethers thereof, $CO_2H$ and esters thereof, and amides and tertiary amines of $CH_2NH_2$.

3. The process in accordance with claim 1, wherein the dienophile is selected from the group consisting of maleic anhydride, maleic acid, maleate esters, fumaric acid, fumarate esters, maleimides, acrylic acid, acrylate esters, and acrolein.

4. The process in accordance with claim 1, wherein the solvent is selected from the group consisting of the furanic, ethers, esters, aromatics, heteroaromatics, aliphatic, nitriles, ketones, alcohols, amides, sulfoxides, and nitrated and chlorinated.

5. The process in accordance with claim 1, wherein the dienophile and the furanic are led into the continuous reactor in a molar ratio in the range 5:1 to 1:5.

6. The process in accordance with claim 1, wherein the furanic comprises 2-methylfuran, the dienophile comprises maleic anhydride and the solvent comprises methyl tert-butyl ether which are led into the continuous reactor while maintaining the temperature of the first liquid feed stream, the second fluid feed stream and the reaction mixture in the continuous reactor above the crystallization temperature of maleic anhydride.

7. An apparatus for the continuous preparation of a cycloadduct product from the reaction of a furanic with a dienophile in accordance with claim 1, said apparatus comprising:

a first feed vessel comprising a first feed outlet and a first heating device;

a second feed vessel comprising a second feed outlet;

a continuous reactor comprising a reactor inlet that is connected to the first and the second feed outlets and further comprising a reactor outlet;

a product isolation zone comprising a product inlet that is connected to the reactor outlet and further comprising a product outlet.

8. The apparatus in accordance with claim 7, wherein the continuous reactor comprises a continuous stirred-tank reactor (CSTR), a fluidized bed reactor, a spinning disc reactor (SDR), an optionally pulsed helical tube reactor, an optionally pulsed oscillating baffled reactor (OBR) and/or a plug flow reactor.

9. The apparatus in accordance with claim 7, wherein the product isolation zone comprises a (semi-)continuous crystallizer and a solid-liquid separation device, wherein said continuous crystallizer comprises the product inlet that is connected to the reactor outlet.

10. The apparatus in accordance with claim 7, wherein the product isolation zone is integrated into the continuous reactor.

11. The apparatus in accordance with claim 7 wherein the product outlet is connected to a product storage vessel and to a liquid storage vessel.

12. The process in accordance with claim 1, wherein the furanic comprises furan, 2-methylfuran or 2,5-dimethylfuran.

13. The process in accordance with claim 1, wherein the dienophile is maleic anhydride.

14. The process in accordance with claim 6, wherein the furanic comprises 2-methylfuran, the dienophile comprises maleic anhydride and the solvent comprises methyl tert-butyl ether which are led into the continuous reactor while maintaining the temperature in the range of 30-100° C.

15. The process in accordance with claim 6, wherein the furanic comprises 2-methylfuran, the dienophile comprises maleic anhydride and the solvent comprises methyl tert-butyl ether which are led into the continuous reactor while maintaining the temperature in the range of 40-70° C.

16. The process in accordance with claim 1, wherein the first liquid feed stream comprises the dienophile and the solvent in which the dienophile is dissolved, and wherein the solvent is the furanic.

* * * * *